(12) United States Patent
Grainger et al.

(10) Patent No.: US 10,550,304 B2
(45) Date of Patent: Feb. 4, 2020

(54) QUATERNARY AMMONIUM COMPOUNDS AND GAS HYDRATE INHIBITOR COMPOSITIONS

(71) Applicant: M-I DRILLING FLUIDS UK LIMITED, Aberdeen (GB)

(72) Inventors: Neil Grainger, Aberdeen (GB); Neil David Feasey, Basingstoke (GB)

(73) Assignee: M-I Drilling Fluids UK Limited, Aberdeen (GB)

(*) Notice: Subject to any disclaimer, the term of this patent is extended or adjusted under 35 U.S.C. 154(b) by 0 days.

(21) Appl. No.: 14/909,402

(22) PCT Filed: Jul. 31, 2014

(86) PCT No.: PCT/GB2014/052347
§ 371 (c)(1),
(2) Date: Feb. 1, 2016

(87) PCT Pub. No.: WO2015/015211
PCT Pub. Date: Feb. 5, 2015

(65) Prior Publication Data
US 2016/0186033 A1    Jun. 30, 2016

(30) Foreign Application Priority Data

Aug. 1, 2013    (GB) .................................. 1313807.8

(51) Int. Cl.
*C09K 8/035*    (2006.01)

(52) U.S. Cl.
CPC .......... *C09K 8/035* (2013.01); *C09K 2208/22* (2013.01)

(58) Field of Classification Search
None
See application file for complete search history.

(56) References Cited

U.S. PATENT DOCUMENTS

| | | | |
|---|---|---|---|
| 3,034,907 A | 5/1962 | Alois et al. | |
| 4,165,239 A | 8/1979 | Linden et al. | |
| 5,705,603 A | 1/1998 | Krull et al. | |
| 6,004,913 A * | 12/1999 | Iacobucci ............... | A61K 8/416 510/123 |
| 6,008,158 A | 12/1999 | Hasebe et al. | |
| 6,528,070 B1 | 3/2003 | Bratescu et al. | |
| 6,596,911 B2 | 7/2003 | Przybylinski et al. | |
| 7,183,240 B2 | 2/2007 | Dahlmann et al. | |
| 8,034,748 B2 | 10/2011 | Dahlmann et al. | |
| 2004/0163307 A1 | 8/2004 | Dahlmann et al. | |
| 2005/0081714 A1* | 4/2005 | Panchalingam ......... | C09K 8/52 95/153 |
| 2005/0169877 A1 | 8/2005 | Grollier et al. | |
| 2006/0142172 A1* | 6/2006 | Cioletti .................. | C09K 8/524 510/365 |
| 2008/0096777 A1 | 4/2008 | Costello et al. | |
| 2009/0057616 A1 | 3/2009 | Leinweber et al. | |
| 2011/0166048 A1 | 7/2011 | Merli et al. | |
| 2012/0171263 A1 | 7/2012 | Romeu et al. | |
| 2013/0225859 A1 | 8/2013 | Allen et al. | |
| 2013/0319447 A1 | 12/2013 | Albert et al. | |
| 2016/0008251 A1 | 1/2016 | Rose et al. | |
| 2016/0023989 A1 | 1/2016 | Allen et al. | |
| 2016/0186033 A1 | 6/2016 | Grainger et al. | |

FOREIGN PATENT DOCUMENTS

| | | |
|---|---|---|
| CH | 249005 A | 5/1947 |
| CN | 1389291 A | 1/2003 |
| DE | 2511249 A1 | 9/1975 |

(Continued)

OTHER PUBLICATIONS

International Search Report and Written Opinion issued in International Application No. PCT/GB2014/052347; dated Dec. 10, 2014 (12 pages).
STIC Search Result provided by US Patent and Trademark Office on Jun. 18, 2019.
Anonymous, "A new high-spreading ester emollient for the hair care market", Kenneth Mason Publications Ltd., Research Disclosure, 2006, 510 (Oct.), pp. 1302-1303.
Search Report for the equivalent UK patent application 1313807.8 dated Feb. 3, 2014.
Examination Report for the equivalent Australian patent application 2014298215 dated Mar. 16, 2016.
Office Action for the equivalent Canadian patent application 2912507 dated Nov. 24, 2016.

(Continued)

*Primary Examiner* — Jeffrey D Washville

(57) ABSTRACT

Quaternary ammonium compounds and compositions comprising the compounds are disclosed. The compositions are valuable as gas hydrate inhibitors in the oil and gas exploration, recovery and processing industries. The compounds and compositions may have improved biodegradability and reduced toxicity when compared with benchmark materials. Quaternary ammonium compounds of the present disclosure have the formula (I) in which R is $C_{1-4}$ alkyl, $C_{6-10}$ aryl, or $C_{1-4}$alkyl-$C_{6-10}$aryl; $R^1$ is hydrogen or a group of formula —C(=O)X; and $R^2$ is hydrogen or a group of formula —C(=O)Y, provided that $R^1$ and $R^2$ are not both hydrogen; X and Y are each independently a hydrogen, $C_{1-6}$ alkyl or $C_{1-6}$ alkenyl group, and Z is a $C_{4-24}$ alkyl or $C_{4-24}$ alkenyl group; each D is independently $C_{1-4}$ alkylene; and $A^-$ is an anion.

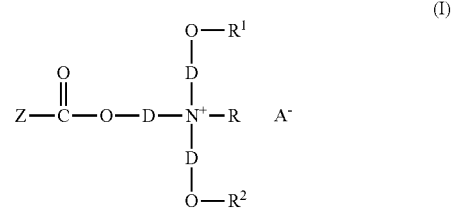

15 Claims, No Drawings

(56) References Cited

FOREIGN PATENT DOCUMENTS

| | | |
|---|---|---|
| DE | 2522014 A1 | 12/1975 |
| DE | 2728237 A1 | 1/1979 |
| DE | 3608212 A1 | 9/1987 |
| DE | 3608244 A1 | 9/1987 |
| EP | 0295385 A1 | 12/1988 |
| EP | 1026220 A1 | 8/2000 |
| HU | 167813 B | 12/1975 |
| HU | 175509 B | 8/1980 |
| HU | 182979 B | 3/1984 |
| HU | 188521 B | 10/1984 |
| JP | 05093181 A | 4/1993 |
| JP | 2006282566 A | 10/2006 |
| JP | 2008063374 A | 3/2008 |
| RU | 2043491 C1 | 9/1995 |
| RU | 2195464 C1 | 12/2002 |
| WO | 95/17579 A1 | 6/1995 |
| WO | 96/34177 A1 | 10/1996 |
| WO | 2000/65010 A1 | 11/2000 |
| WO | 2005116399 A1 | 12/2005 |
| WO | 2010128313 A2 | 11/2010 |
| WO | 2012/061093 A1 | 5/2012 |
| WO | 2013/147092 A1 | 10/2013 |
| WO | 2014/146991 A1 | 9/2014 |

OTHER PUBLICATIONS

Substitute Examination Report for the equivalent Malaysian patent application PI 2015704190 dated Mar. 18, 2019.

* cited by examiner

QUATERNARY AMMONIUM COMPOUNDS AND GAS HYDRATE INHIBITOR COMPOSITIONS

TECHNICAL FIELD

The present disclosure relates to quaternary ammonium compounds and compositions comprising the compounds. The compositions are useful for inhibiting formation of gas hydrates in the oil and gas exploration, recovery and processing industries.

BACKGROUND

At high pressure and low temperature water within pipelines can form gas hydrates as a result of interaction with low molecular weight gases present, such as methane and ethane. Such gas hydrates can form plugs and result in lost production (and revenue) and cause safety issues in the oilfield industry. Amelioration of such problems may be undertaken by dehydration, heating (such as direct electrical heating) and chemical inhibition of the hydrate formation. Thermodynamic inhibitors (THIs) such as methanol and ethylene glycol are frequently used but require large volumes for treatment so are generally undesirable at least in terms of cost. This high volume requirement relating to THIs can also be particularly problematic for offshore deepwater production.

Low dose hydrate inhibitors (LDHIs) have been developed and applied in oil and gas production as an alternative to the THIs mentioned above. These LDHIs can be divided into two broad subclasses; kinetic hydrate inhibitors (KHIs), and anti-agglomerants (AAs). KHIs act mainly as gas hydrate anti-nucleation compounds (although they may also inhibit gas hydrate crystal growth). Typically KHIs operate at lower subcooling values than AAs. "Subcooling" is the difference between the operating temperature and the temperature at which hydrates first start to form (the hydrate equilibrium temperature) at a given pressure. Higher values of subcooling means that the compounds are able to inhibit hydrate formation at lower temperatures (for a given pressure). KHIs are normally considered to provide time limited protection at subcooling values to around 12° C.

Anti-agglomerants (AAs) can function at higher subcoolings. In contrast to KHIs they allow gas hydrates to form but generate a slurry of dispersed hydrate particles in the liquid hydrocarbon that remains mobile and does not result in a plug forming.

The first AAs were developed by Shell based on quaternary ammonium compounds as described in WO 95/17579 and WO 96/34177. Other chemistries have been described as providing effective AAs, mostly based on quaternary ammonium/phosphonium based molecules (Kelland, M. A., Energy & Fuels, 2006, 20, 825-847 and Kelland, M., Production Chemicals for the Oil and Gas Industry; CRC Press, Boca Raton, Fla., 2009). There is typically a limitation on the fraction of water present in the liquid phase—above a certain amount the hydrate droplets will not flow within the oil phase, the resulting slurry being too viscous (Sloan, E. D. et al., Natural Gas Hydrates in Flow Assurance, Gulf Professional Publishing, Burlington, Mass., 2011, and Anklam, M. A. et al., AIChE Journal, 2008, 54, 565-574). Many AA LDHIs are also limited in that they often exhibit relatively poor environmental compatibility.

WO 2005/116399 and U.S. Pat. No. 6,596,911 describe onium (such as quaternary ammonium) LDHI AA compounds which may include heteroatoms in the alkyl chains (especially the longest chain) attached to the central atom.

U.S. Pat. Nos. 7,183,240 and 8,034,748 describe LDHI AA compounds based on a quaternary ammonium structure in which the chains attached to the central atom contain alkylene oxide units.

SUMMARY

The present disclosure provides quaternary ammonium compounds, which may be useful as gas hydrate inhibitors, and more particularly as gas hydrate anti-agglomerants (AAs). Compounds of the present disclosure are not only effective gas hydrate inhibitors, but may also display improved biodegradability and reduced toxicity, particularly in aqueous or marine environments, when compared with benchmark materials.

According to one aspect, the present disclosure provides a quaternary ammonium compound of formula (I)

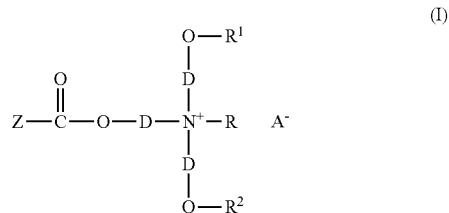

wherein:

R is a $C_{1-4}$ alkyl group, $C_{6-10}$ aryl group, or $C_{6-10}$aryl group, poly($C_{2-4}$ alkylene oxide), or poly(styrene oxide), any of which may be substituted by one or more groups selected from halide, $C_{1-4}$ alkyl, —OH, —COOH, —C(=O)$C_{1-4}$alkyl, or $C_{1-4}$alkylene—OH;

$R^1$ is hydrogen or a group of formula —C(=O)X; and $R^2$ is hydrogen or a group of formula —C(=O)Y, provided that $R^1$ and $R^2$ are not both hydrogen;

X and Y are each independently a hydrogen, $C_{1-6}$ alkyl or $C_{1-6}$ alkenyl group;

Z is a $C_{4-24}$ alkyl or $C_{4-24}$ alkenyl group;

each D is independently a $C_1$ to $C_4$ alkylene group; and $A^-$ is an anion.

Also described are mixtures comprising quaternary ammonium compounds according to formula I. Particularly, these quaternary ammonium compounds or mixtures of compounds may be useful as AA LDHI compounds.

A further aspect relates to anti-agglomeration hydrate inhibitor compositions comprising a quaternary ammonium compound or mixture of compounds as defined herein (e.g. of formula I).

The present disclosure also relates to methods of inhibiting gas hydrate agglomeration in a liquid. The methods comprise contacting the liquid with an AA composition as described herein.

A further aspect relates to the use of the compositions defined herein in oil and gas exploration, recovery, or processing applications.

Further Definitions; Options and Preferences

The quaternary ammonium compounds described herein and compositions comprising them demonstrate good gas hydrate inhibition properties. The quaternary ammonium compounds may also have improved biodegradability and/or lower toxicity when compared with known benchmark compounds (such as tributyl tetradecylphosphonium chloride (TTPC)).

In the compounds described herein, particularly R may be a $C_{1-4}$ alkyl or $C_{1-4}$alkyl-$C_{6-10}$aryl group; more particularly R may be a $C_{1-2}$ alkyl group or $C_{1-2}$alkyl-$C_{6-10}$aryl group; more particularly R may be $C_{1-2}$ alkyl or benzyl, more particularly R may be a methyl group. The R group may be substituted by one or more groups selected from halide, $C_{1-4}$ alkyl, —OH, —COOH, —C(=O)$C_{1-4}$ alkyl, or $C_{1-4}$alkylene—OH; more particularly halide, $C_{1-4}$ alkyl or —OH, more particularly $C_{1-4}$ alkyl (e.g. methyl, ethyl, propyl or butyl; more particularly ethyl) or —OH. In some aspects the R group is unsubstituted. Compounds in which R is a methyl group may impart improved gas hydrate inhibition properties to compositions comprising the compounds.

In some aspects, one of $R^1$ or $R^2$ may be hydrogen with the other being —C(=O)X or —C(=O)Y respectively, i.e. the quaternary ammonium compound may be a diester. In preferred aspects, $R^1$ is —C(=O)X and $R^2$ is —C(=O)Y, i.e. the quaternary ammonium compound is a triester. The $R^1$ and $R^2$ groups are not both hydrogen atoms, i.e. the quaternary ammonium compound is not a monoester. This is because the diester and triester compounds of formula I and compositions comprising them have been found to show good anti-agglomeration properties as hydrate inhibitors which may not be demonstrated, or only to a lesser degree, by the monoester compounds and compositions comprising them. The preferred triester compound may be present in admixture with one or more diester components as mentioned herein. In this situation, in some aspects the mixture may contain more triester than diester component, e.g. the composition may contain greater than about 50 mol. %, more particularly greater than 65 mol. %, more particularly greater than 80 mol. % of a triester compound or mixture of compounds according to formula I. Alternatively, in some aspects the mixture may contain more diester than triester component, e.g. the composition may contain greater than about 50 mol. %, more particularly greater than 65 mol. %, more particularly greater than 80 mol. % of a diester compound or mixture of compounds according to formula I.

X and Y may particularly each independently be $C_{1-6}$ alkyl or $C_{1-6}$ alkenyl. More particularly X and Y may be $C_{1-6}$ alkyl, more particularly $C_{2-6}$ alkyl, more particularly $C_3$ or $C_4$ alkyl, more particularly $C_3$ alkyl. The X and Y groups may independently be straight chain or branched chain alkyl groups such as methyl, ethyl, propyl, propyl, n-butyl, i-butyl, sec-butyl, t-butyl, n-pentyl, i-pentyl, t-pentyl, neo-pentyl, sec-pentyl, hexyl, and i-hexyl; in some preferred aspects, the X and Y groups are independently selected from propyl, n-butyl, n-pentyl and i-hexyl. Independently of the nature of the X and Y groups, in preferred compounds, the X and Y groups are the same. Particularly the X and Y groups may both be straight chain $C_3$ alkyl groups.

Z may particularly be $C_{4-24}$ alkyl or $C_{4-24}$ alkenyl, particularly $C_{5-21}$ alkyl or $C_{5-21}$ alkenyl, particularly $C_{7-17}$ alkyl or $C_{7-17}$ alkenyl, particularly $C_{11-13}$ alkyl or $C_{11-13}$ alkenyl, more particularly $C_{11}$ or $C_{13}$ alkyl or alkenyl, more particularly $C_{13}$ alkyl or alkenyl. The —C(=O)—Z group may be the acyl unit derived from a fatty acid e.g. the acyl unit from caprylic acid, capric acid, lauric, myristic, palmitic, stearic, oleic, erucic, linoleic acid, linolenic acid, and behenic acid.

Preferably the carbon chain of Z is longer than that of any of X and Y that are present in the same compound.

Although, the alkyl or alkenyl groups, X, Y and Z, may be straight or branched, straight chains are preferred. Where it is an alkenyl group, this may particularly have 1, 2 or 3 double bonds, particularly 1 or 2 double bonds, particularly one double bond.

D may particularly be a $C_2$ alkylene group, i.e. —$CH_2CH_2$—.

One example of the quaternary ammonium compound includes a cation having formula (II) or (III) below:

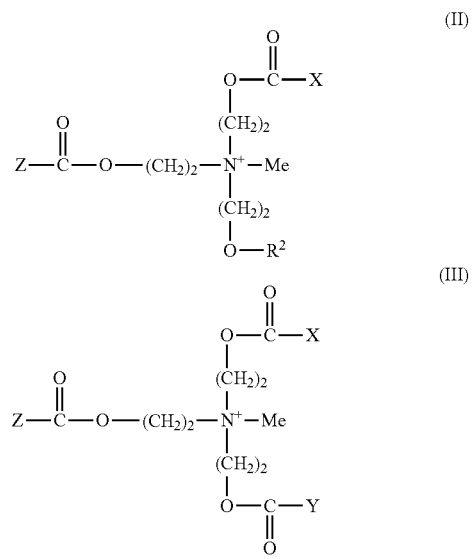

Wherein the options and preferences for $R^2$, X, Y and Z are as defined above.

Another example of quaternary ammonium compound of the present disclosure includes a cation having formula (IV) below:

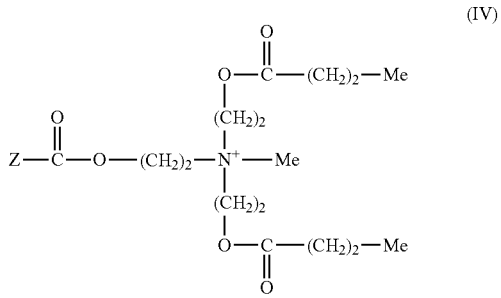

Wherein the options and preferences for Z are as defined above.

Mixtures of quaternary ammonium compounds each according to any of formulae I, II, III and/or IV are also envisaged. Particularly preferable are mixtures of quaternary ammonium compounds in which the ratio of chain lengths in the —C(=O)—Z groups in the mixture corresponds to the ratio of chain lengths in the acyl groups in a fatty acid mixture, e.g. a fatty acid mixture used to manufacture the mixture of quaternary ammonium compounds. For example, preferably the ratio of chain lengths in the —C(=O)—Z groups in the mixture of quaternary ammonium compounds corresponds (particularly to at least 90% correspondence, particularly at least 95%, more particularly at least 99%, more particularly at least 99.9%) to the ratio of chain lengths in the acyl groups in a vegetable fatty acid mixture such as a fatty acid mixture selected from rapeseed oil fatty acids, soya oil fatty acids, tall oil fatty acids, tallow oil fatty acids, palm oil fatty acids, palm kernel oil fatty acids, coconut oil fatty acids, stripped coconut oil fatty acids, cottonseed oil fatty acids, wheat germ oil fatty acids, olive oil fatty acids, corn oil fatty acids, sunflower oil fatty acids, safflower oil fatty acids, and hemp oil fatty acids. Particularly the fatty acid mixture may be selected from rapeseed oil fatty acids, soya oil fatty acids, tall oil fatty acids, palm oil fatty acids, coconut oil fatty acids and stripped coconut oil fatty acids. The values of correspondence levels of at least 90%, at least 95%, at least 99% and at least 99.9% refer to the sum of the percentage content differences for each fatty acid component in a standard definition of the oil and the fatty acid acyl groups in the mixture, i.e. calculated by comparing the percentage content for each fatty acid chain length component, calculating the difference in percentage content values and summing these differences.

In some aspects, at least 90%, particularly at least 95%, of the quaternary ammonium compounds in the mixture have —C(=O)—Z acyl groups with a carbon chain length selected from $C_8$ and $C_{10}$, $C_{10}$ and $C_{12}$, $C_{12}$ and $C_{14}$, $C_{14}$ and $C_{16}$, $C_{16}$ and $C_{18}$, or $C_{18}$ and $C_{20}$. Particularly the carbon chain lengths may be selected from $C_8$ and $C_{10}$, $C_{12}$ and $C_{14}$, or $C_{16}$ and $C_{18}$; more particularly $C_{12}$ and $C_{14}$.

In preferred aspects, the ratio of chain lengths in the —C(=O)—Z groups in the mixture of quaternary ammonium compounds corresponds to at least one of the fatty acid mixtures shown in the table below. Particularly the level of correspondence (i.e. the total difference in percentage amounts from the percentages listed in the table below) may be at least 90%, particularly at least 95%, more particularly at least 99%, more particularly at least 99.9%.

of quaternary ammonium compounds. Stripped coconut fatty acid is a mixture of similar fatty acid components to coconut fatty acid but with the amounts of higher and lower molecular weight components reduced. The main fatty acid components are as for coconut fatty acid but with reduced amounts of caprylic (octanoic), capric (decanoic), and partially unsaturated octadecanoic (containing one and two double bonds) acids.

The anion $A^-$ included in the quaternary ammonium compound is not particularly limited. Generally the nature of this ion will depend on the method by which the quaternary ammonium compound is produced. Examples include halides, particularly chloride, methosulphate, methophosphate, and ethosulphate. More particularly the anion $A^-$ may be methosulphate ($MeSO_4^-$). Advantages in terms of anti-agglomeration performance may be observed particularly when the methosulphate anion is used.

Particularly preferred mixtures of quaternary ammonium compounds are mixtures in which each compound conforms to formula IV above, particularly those in which the —C(=O)—Z groups are the acyl groups derived from coconut fatty acid, stripped coconut fatty acid or a mixture of $C_{12}$ and $C_{14}$ fatty acids. Also preferred are compounds of formula IV in which the Z group is a straight chain $C_{13}$ alkyl group.

In another aspect, the present disclosure provides a method of producing the quaternary ammonium compounds described herein. The method comprises esterifying a trialkanolamine followed by quaternisation. In a first step, a trialkanolamine such as triethanolamine, tripropanolamine, or tributanolamine, particularly triethanolamine, is subjected to an esterification step which can be carried out with a fatty acid, XCOOH, YCOOH, ZCOOH or mixtures or suitable

| Fatty acid mixture | Carbon chain length distribution of fatty acids (%) | | | | | | | | | | |
|---|---|---|---|---|---|---|---|---|---|---|---|
| | C6 | C8 | C10 | C12 | C14 | C16 | C18 | C18:1 | C18:2 | C20 | C22 |
| Coco | | 7.6 | 6.1 | 46 | 18.7 | 10 | 2.9 | 6.8 | 1.4 | | |
| Stripped coco | | 0.4 | | 55.4 | 19.6 | 9.5 | 4.4 | 1.4 | | | |
| C16/C18 | | | | | 1.3 | 28.7 | 67.2 | | | 1.7 | |
| C8/C10 | 0.1 | 56.4 | 43.3 | 0.2 | | | | | | | |
| C12/C14 | | | 1 | 68 | 28 | | 3 | | | | |

"coco" = coconut fatty acid
"stripped coco" = stripped coconut fatty acid

Particularly the ratio may correspond to the fatty acid mixture "coco", "stripped coco" or "C12/C14" in the above table. Particularly the ratio may correspond to the fatty acid mixture "coco" in the table above.

In preferred mixtures of quaternary ammonium compounds, the groups —C(=O)—Z correspond broadly to the acyl groups of coconut oil fatty acid. Thus, preferred mixtures of the present disclosure are those comprising multiple compounds of formulae I, II, III and/or IV above, in which the —C(=O)—Z groups in the mixture have acyl groups derived from lauric acid (dodecanoic acid) as the predominant component, with smaller amounts of acyl groups from caprylic (octanoic), capric (decanoic), myristic (tetradecanoic), palmitic (hexadecanoic), stearic (octadecanoic) and partially unsaturated octadecanoic (containing one and two double bonds), ricinoleic, isostearic, isopalmitic, eicosanoic, gadoleic, palmitoleic, arachidonic, and clupanadonic, acids also present.

The acyl groups of stripped coconut acid are also preferred options for the —C(=O)—Z groups in the mixtures derivatives thereof, such as acid chloride or acid anhydride. Preferably the fatty acid component is a mixture of fatty acids. This mixture may particularly comprise the fatty acids in the ratios corresponding to the X, Y and Z groups in the final product. For example, the fatty acid component may include butyric acid and coconut fatty acid in a 2:1 mixture to obtain an eventual product in which —C(=O)—X and —C(=O)—Y are the acyl component from butyric acid, and —C(=O)—Z is the acyl component from coconut fatty acid.

Particularly, the fatty acid component may be used in excess or at least in about a 3:1 molar ratio (e.g. at least 2.9:1 molar ratio) with the trialkanolamine to encourage triesterification. In individual molecules, esterification may of course only proceed to produce the monoester or diester due to local differences in reagent concentrations or conditions. The overall ratio of fatty acid component to trialkanolamine can be used to exert some control over the level of esterification in the final product. For example, a 2:1 molar ratio of fatty acid component to trialkanolamine would encourage a higher proportion of the diester compounds in the product. As noted above, an excess or at least 3:1 molar ratio of fatty acid or fatty acid mixture to trialkanolamine is preferred to encourage triesterification.

After esterification the resulting tertiary amine compound is quaternised through the action of an alkylating agent. Examples of suitable alkylating agents include methyl chloride and dimethyl sulphate. Particularly the alkylating agent may be dimethyl sulphate. Other suitable quaternising agents include halides, such as chloride, iodide or bromide; hydroxides; sulphonates; alkyl sulphates (e.g. dimethyl sulphate); sultones; phosphates; $C_{1-12}$ alkylphosphates; $C_{1-12}$ alkylphosphates; borates; $C_{1-12}$ alkylborates; nitrites; nitrates; carbonates; bicarbonates; alkanoates; O,O-di $C_{1-12}$ alkyldithiophosphates; or mixtures thereof. By their use to form the quaternary ammonium compounds, these quaternising agents also define preferences for the corresponding anions $A^-$ and the R group herein.

Particularly the quaternising agent may be derived from dialkyl sulphates (e.g. dimethyl sulphate), N-oxides, sultones (e.g. propane and butane sultones); alkyl, acyl or araalkyl halides (e.g. methyl and ethyl chloride, bromide or iodide or benzyl chloride), and hydrocarbyl or alkyl substituted carbonates. If the acyl halide is benzyl chloride, the aromatic ring may be further substituted with $C_{1-6}$ alkyl or alkenyl groups. The hydrocarbyl (or alkyl) groups of the hydrocarbyl substituted carbonates may contain 1-50, 1-20, 1-10 or 1-5 carbon atoms per group. In one aspect the hydrocarbyl substituted carbonates contain two hydrocarbyl groups that may be the same or different. Examples of suitable hydrocarbyl substituted carbonates include dimethyl or diethyl carbonate.

In some aspects the quaternising agent can be a hydrocarbyl epoxide (e.g. styrene oxide, ethylene oxide, propylene oxide, butylene oxide, stilbene oxide and $C_{2-50}$ epoxide).

As noted above, by their use to form the quaternary ammonium compounds, these quaternising agents also define preferences for the corresponding anions $A^-$ and the R group herein.

In another aspect, the present disclosure provides a gas hydrate inhibitor composition (e.g., an anti-agglomeration composition) comprising a quaternary ammonium compound of the present disclosure. The composition may contain a mixture of quaternary ammonium compounds as described herein. Such compositions may comprise the quaternary ammonium compound(s) and a solvent. The solvent may be selected from organic solvents such as an aromatic organic solvent, e.g. benzene, or alkyl benzenes such as toluene or xylene, or mixtures of aromatic organic solvents, e.g. a mixture of $C_{10}$ and $C_{12}$ alkyl benzenes (e.g. "Solvesso 150"®), and also non-aromatic solvents, such as alcohols (e.g. $C_1$-$C_6$ alcohols such as isopropyl alcohol, ethylene glycol, or propylene glycol, or mixtures thereof). Non-organic solvents may also be useful, e.g. water either alone or with a water miscible organic solvent to assist in the dispersion and/or dissolution of the quaternary ammonium compound. Examples of suitable water miscible solvents include $C_1$-$C_6$ alcohols such as isopropanol, ethylene glycol or propylene glycol, or mixtures thereof. However, preferred solvents are alkoxy alcohols, especially 2-butoxyethanol.

Particularly the composition of this aspect of the present disclosure may contain more than 10% by volume of the quaternary ammonium compound or mixture of compounds as defined herein, particularly between about 10 and 99% by volume, particularly from about 25 to about 90%. In some aspects, the compositions may contain up to about 50% by volume of the quaternary ammonium compound or mixture of compounds as defined herein and in some aspects possibly even more. For example the composition may contain 90% by volume of the quaternary ammonium compound or mixture of compounds as defined herein in 10% by volume of solvent as defined herein (e.g. IPA).

The gas hydrate inhibitor composition of this aspect optionally includes other ingredients. For instance, the composition may include a water miscible organic solvent to assist in the dispersion and/or dissolution of the quaternary ammonium compound as noted above. This solvent component may be present at a level of up to 30 volume percent of the composition, typically 5 to 30 volume percent. Particularly, it may be present at a level not more than 20 volume percent, most particularly at a level of 10 to 20 volume percent.

In use, the compositions of the present disclosure become diluted and the quaternary ammonium compound (or mixture of quaternary ammonium compounds) may particularly be present at a level of about 0.25 to about 10 volume %, particularly about 0.5-5 volume %, more particularly about 2-4 volume % based on the amount of water in the system (not on the overall amount of liquid components). If too much of the quaternary ammonium compound (or mixture) is used, any additional benefit is outweighed by the additional cost of the materials. If insufficient quaternary ammonium compound (or mixture) is used the hydrate inhibition effect is weaker or not observed at all.

The quaternary ammonium compounds (and mixtures or compositions comprising the compounds) may have improved biodegradability and reduced toxicity, particularly in aqueous or marine environments, when compared with benchmark materials.

The toxicity of a quaternary ammonium compound or an LDHI composition comprising the quaternary ammonium compound may be evaluated by testing against *Skeletonema costatum* and determining $EC_{50}$ values in the aquatic environment. Also the percentage biodegradation may be measured after 28 days in seawater. Quaternary ammonium compounds and LDHI compositions may have a *Skeletonema Costatum* toxicity $EC_{50}$ value of greater than 0.1 mg/l, particularly greater than 0.5 mg/l, particularly greater than 1 mg/l, more particularly greater than 2 mg/l.

Quaternary ammonium compounds and LDHI compositions of the present disclosure may have a percentage biodegradation in seawater after 28 days of greater than 20%, particularly greater than 25%, particularly greater than 30%, more particularly greater than 40%, most particularly greater than 50% or greater than 60%.

These options in terms of toxicity and biodegradation are particularly achievable when the quaternary ammonium compounds and mixtures have a Z group that is longer than the X and Y groups, in particular when the —C(=O)—Z group is derived from the acyl group of coconut fatty acid, stripped coconut fatty acid, or is an acyl group of 12 carbon atoms, 14 carbon atoms or a mixture thereof.

In a further aspect, the present disclosure relates to a method of inhibiting gas hydrate agglomeration in a liquid. The method comprises adding a composition comprising a quaternary ammonium compound, or mixture of compounds, as defined herein to the liquid. Addition of the composition disclosed herein may result in the liquid having a sub-cooling value of at least 12° C., at least 13° C., at least 14° C., at least 15° C., at least 16° C., at least 17° C. or even more than 18° C. These sub-cooling values may be comparable with or higher than those obtainable with known LDHI compositions.

In a further aspect, the present disclosure relates to the use of a gas hydrate inhibitor composition as described herein, or a process as described herein, to inhibit agglomeration of gas hydrates in oil and/or gas production or in a downhole or oilfield application, e.g. in a wellbore application, such as an oil drilling application, or subterranean application. In some embodiments this process comprises contacting a fluid stream (e.g. a fluid stream comprising oil and/or gas) with a gas hydrate inhibitor compound or composition as described herein, or using a process as described herein, to reduce gas hydrate agglomeration rates in the production or wellbore operation. This "contacting" with a fluid stream typically involves addition of the gas hydrate inhibitor compound or composition to the fluid stream, e.g. at an amount as described herein.

It will be appreciated that the compounds, compositions and processes of the present disclosure are useful during the course of oil and gas production operations, as well as subterranean operations such as the drilling, cementing, fracturing, maintenance and production, workover, abandonment of a well and other operations associated with subterranean wells.

In the usual way, features that are described herein in relation to one aspect or embodiment are equally applicable to other aspects and embodiments described herein where practically feasible and compatible. Also in respect of numerical ranges disclosed in the present description it will of course be understood that in the normal way the technical criterion for the upper limit is different from the technical criterion for the lower limit, i.e. the upper and lower limits are intrinsically distinct proposals.

Embodiments of the present disclosure are described below by way of example only, and with reference to the accompanying figures.

EXAMPLES

Synthetic Example 1

Esterification 300 g of butyric acid (2 moles) and 384 g of myristic acid (1 mole) were introduced in an inert atmosphere into a glass reactor, 263 g of triethanolamine (1.03 moles) were added with stirring. The mixture was heated for at least 24 h at 140-155° C. in order to remove the water of the reaction. The progress of the reaction was monitored by an acid/base assay which determines the residual acidity to obtain an esterification of at least 95% of the fatty acids.

855 g of a brown liquid product, referred to as "esteramine 1" were recovered, consisting essentially of a mixture of unesterified fatty acids and mono-, di- and triesterified amine (small amount of unreacted triethanolamine).

Quaternization 186 g of dimethyl sulphate were added with stirring at a temperature of 60-90° C. to 732 g of "esteramine 1". After one hour of digestion, the virtually complete absence of residual amine was verified by acid/base assay.

The product was then diluted to 90% by adding approximately 101 g of isopropanol. 1019 g of the product "X3342-C14" were obtained.

The product is predominantly a triester compound with smaller amounts of mono- and di-esters present.

Compounds

The following compounds in Table 1 were obtained for testing in gas hydrate inhibitor compositions. These compounds were produced by the same reaction as in Synthetic Example 1 but with the initial myristic acid component replaced by a fatty acid or fatty acid mixture having the relevant chain length. The references X, Y, Z, R, and $A^-$ refer to the groups in Formula I above.

TABLE 1

| Product number | Fatty acid from which acyl group is derived | | | Anion | |
|---|---|---|---|---|---|
| | X | Y | Z | R | $A^-$ |
| X3321 | Stripped coco | Butyric | Butyric | Me | MS |
| X3342 | Coconut | Butyric | Butyric | Me | MS |
| X3341 | Stripped coco | Butyric | Butyric | Salt with butyric acid | |
| X3343 | Coconut | Butyric | Butyric | Salt with butyric acid | |
| X3620 | C16/C18 | Butyric | Butyric | Me | MS |
| X3621 | C8/10 | Butyric | Butyric | Me | MS |
| X3622 | C12/C14 | Butyric | Butyric | Me | MS |
| X3342-C10 | C10 | Butyric | Butyric | Me | MS |
| X3342-C12 | C12 | Butyric | Butyric | Me | MS |
| X3342-C14 | C14 | Butyric | Butyric | Me | MS |

"Stripped coco" = stripped coconut fatty acid
"Coconut" = coconut fatty acid
MS = methosulphate The distribution of the carbon chain lengths in the various fatty acid components used in table 1 is shown in table 2.

TABLE 2

| Fatty acid mixture | Carbon chain length distribution of fatty acids (%) | | | | | | | | | | |
|---|---|---|---|---|---|---|---|---|---|---|---|
| | C6 | C8 | C10 | C12 | C14 | C16 | C18 | C18:1 | C18:2 | C20 | C22 |
| Coco | | 7.6 | 6.1 | 46 | 18.7 | 10 | 2.9 | 6.8 | 1.4 | | |
| Stripped coco | | 0.4 | | 55.4 | 19.6 | 9.5 | 4.4 | | 1.4 | | |
| C16/C18 | | | | | 1.3 | 28.7 | 67.2 | | | 1.7 | |
| C8/C10 | 0.1 | 56.4 | 43.3 | 0.2 | | | | | | | |
| C12/C14 | | | | 1 | 68 | 28 | 3 | | | | |

"coco" = coconut oil
"stripped coco" = stripped coconut oil

Anti-Agglomeration (AA) Tests

The AA performance was determined in a rocking cell system—a RCS20 rig obtained from PSL Systemtechnik, Germany. The rig uses ten identical sapphire cells, each with an internal volume of 20 ml. Within each a stainless steel ball moves from end to end as the cells rock and sensors located at either end of the cell measure the run time of the ball. The rocking motion provides mixing and agitation. The rocking system is controlled by computer (rocking angle and rate) and pressure and temperature were logged along with the ball run time. The rocking angle was set to 40° and the frequency to 15 min$^{-1}$.

A synthetic gas composition was used as shown in Table 3. This gas composition is predicted to form Type II gas hydrates.

TABLE 3

| Component | Mol % |
|---|---|
| Methane | 80.40 |
| Ethane | 10.30 |
| Propane | 5.00 |
| i-Butane | 1.65 |
| n-Butane | 0.72 |
| N2 | 0.11 |
| CO2 | 1.82 |

A standard procedure was adopted for all experiments. Cells were charged with brine, test chemical and liquid hydrocarbon (condensate or crude). They were then charged with gas and rocked for 5 minutes until the pressure drop was less than $2 \times 10^5$ Pa (2 Bar). The gas charging to meet this target typically required several repetitions. Rocking then continued for 1 hour at 20° C. with a final repressurisation if the pressure had dropped. Cells were charged to a higher pressure at 20° C. than the required pressure at 4° C. to allow for the pressure drop associated with cooling.

The cells were then cooled to 4° C. at a rate of approximately 4° C. per hour. Once the system reached the set temperature rocking was continued for 12 hours. A shut-in period of 6 hours then followed. During this time the cells were horizontally positioned. At the end of the shut-in rocking was resumed for a further 6 hours.

Brines were prepared using NaCl to provide the required salinity. Two liquid hydrocarbons were used. The first was an additive free condensate obtained from an offshore Netherlands field. The second was an additive free Norwegian crude oil. The crude oil was confirmed as not depositing wax at 4° C.

The four different stages of the test (cooldown, flowing to shut-in, immediate start-up and end test) were assessed by visual inspection and a final overall rating given. The rating criteria used to evaluate the performance on each stage is based on one presented by Shell, which uses a scale from 1 to 5. A ranking of 5 is the best possible score and on occasion may mean there are no visible hydrates in the system at all. A ranking of 1 is a failure while a ranking of 2 represents a marginal hydrate control scenario at best.

The factors used to generate the ranking include crystal morphology, liquid level, phase appearance, type of flow/apparent viscosity and ball movement. Many of these are visually assessed but the movement of the stainless steel ball between the two sensors for each sapphire cell is logged by computer and hence changes can be numerically determined. As an example the factors for a ranking of 1 (test failure) are as follows:

Ranking 1—System failure; pipeline is expected to plug
Deposits on cell's interior surfaces and/or the ball
Large agglomeration of hydrate particles
Multiple phases; one of which will not disperse
Hydrates do not disperse with strong agitation
Low liquid level
Exceedingly high viscosity liquids
Possible stuck ball In contrast a ranking of 5 requires no deposits, hydrate particles—if present—are very fine, an easily dispersible liquid and rapid recovery of flow following the start-up.

Examples 1-5

Standard Conditions

Compositions were tested under standard conditions of $80 \times 10^5$ Pa (80 Bar) gas pressure using the additive free condensate described above. The compounds were present at 2 volume % in a 3 wt. % per unit volume NaCl brine (30 g NaCl per liter). Results are presented in table 4. A benchmark compound, tributyl tetradecylphosphonium chloride (TTPC), was used for comparison.

TABLE 4

| | | Ranking | | | |
|---|---|---|---|---|---|
| Example | Composition | Stage 1 | Stage 2 | Stage 3 | Stage 4 |
| Reference Example 1 | TTPC | 5 | 5 | 5 | 5 |
| Example 1 | X3342 | 4 | 4 | 4 | 4 |
| Example 2 | X3622 | 4 | 4 | 4 | 4 |
| Example 3 | X3342-C10 | 4 | 3+ | 4 | 4 |
| Example 4 | X3342-C12 | 2 | 3+ | 4 | 3+ |
| Example 5 | X3342-C14 | 4 | 5 | 5 | 4 |

Stage 1 = Cooldown
Stage 2 = Flowing and shut-in
Stage 3 = Immediate restart
Stage 4 = Restart to end test It can be seen in table 4 that all of these Example compounds perform at a similar level to the reference compound. The X3342-C12 compound is slightly lower in performance but is still sufficient to be useable in an LDHI composition.

Examples 6-10

Standard Conditions

Further tests were performed under the same standard conditions as used for Examples 1-5 above. In these tests, one overall rating was given covering all of the stages. In some cases two ratings are given where the behaviour of the compound altered significantly during the test. The results are presented in table 5.

TABLE 5

| Example | Composition | Ranking |
|---|---|---|
| Reference Example 2 | X3343 | 1− |
| Reference Example 3 | X3341 | 1+ |
| Example 6 | X3342 | 4 |
| Example 7 | X3321 | 3 |
| Example 8 | X3620 | 2+ |
| Example 9 | X3621 | 5/2− |
| Example 10 | X3622 | 3+ |

A number of comparisons can be drawn from the results in table 5. For example, comparison of examples 8-10 shows an effect of the length of the Z chain in formula I. The compositions in these examples differ only in the length of the Z chain in formula I. The performance seems to progress in the order example 8 (C16/C18)<example 9 (C8/C10) <example 10 (C12/C14). These results indicate that the C12/C14 chain length in example 10 is preferable.

Comparison of example 7 with reference example 3 and also example 6 with reference example 2 highlights the difference in performance between compounds in which the R group in formula I is an alkyl group (Me in both examples 6 and 7) and those in which the group corresponding to R in formula I is H (reference examples 2 and 3).

Comparison of examples 6 and 7 highlights the difference in performance between compounds in which the Z group of formula I is derived from coconut fatty acid (example 6) and those in which the Z group of formula I is derived from stripped coconut fatty acid (example 7). However despite these differences both examples 6 and 7 reflect behaviour of a useful LDHI composition.

Examples 11-13

Varying Conditions

A range of conditions was used to determine performance as shown in Table 6. This range was chosen to represent typical conditions for which an anti-agglomerant composition should be suited.

TABLE 6

| Pressure | $80 \times 10^5$, $120 \times 10^5$ Pa (80, 120 Bar) |
|---|---|
| Water cut (% ratio of water by volume compared to overall liquid components) | 10, 30, 50% |
| Brine salinity | 0, 1.5, 3% |
| Liquid hydrocarbon | Crude, condensate |
| Composition dose rate | 1, 2, 4% |

A range of tests were performed by systematically varying the parameters in table 6. The sets of conditions shown in table 7 were tested for a range of different compositions. Again TTPC was used as a reference AA composition.

TABLE 7

| Condition set | Composition dose rate (%) | Water cut (%) | Salinity (%) | Pressure (Pa) |
|---|---|---|---|---|
| 1 | 1 | 10 | 1.5 | $120 \times 10^5$ (120 Bar) |
| 2 | 2 | 10 | 0 | $80 \times 10^5$ (80 Bar) |
| 3 | 4 | 50 | 1.5 | $80 \times 10^5$ (80 Bar) |
| 4 | 1 | 30 | 3 | $80 \times 10^5$ (80 Bar) |
| 5 | 2 | 50 | 3 | $120 \times 10^5$ (120 Bar) |
| 6 | 1 | 50 | 0 | $80 \times 10^5$ (80 Bar) |
| 7 | 4 | 30 | 0 | $120 \times 10^5$ (120 Bar) |
| 8 | 4 | 10 | 3 | $120 \times 10^5$ (120 Bar) |

Compositions were tested in both crude oil and condensate as described above.

Results were assessed by visual inspection as described above with an overall rating being given for each condition set.

Compositions tested were X3342-C14, X3342, and X3622. For each composition, the number of rankings of level 3 or above was counted for each batch of 8 tests described in table 7. The results are provided in table 8.

TABLE 8

| | | Number of tests (out of 8) at ranking 3 or above | |
|---|---|---|---|
| Example | Composition | Condensate | Crude oil |
| Reference example 4 | TTPC | 5 | 4 |
| Example 11 | X3342-C14 | 6 | 4 |
| Example 12 | X3342 | 5 | 5 |
| Example 13 | X3622 | 4 | 4 |

Examples 11-13 indicate that all three of the compounds tested show effective AA properties and similar behaviour to the TTPC reference example 4 in both crude oil and condensate environments.

A trend was also seen in terms of the water cut. All of the tests apart from one scored a ranking of 2 or lower at water cut values of 50% irrespective of the other conditions. The exception was the X3342-C14 sample which scored a ranking of 3 under condition set 3 in table 7. The other test compounds and the reference compound TTPC scored a ranking of 2 or less under all condition sets in both crude oil and condensate. This is consistent with the behaviour of the test compositions being similar to that of the reference compound and also indicates that a water cut amount of less than 50% may be preferred to obtain the best anti-agglomeration results (although certain compositions may be useable at higher water cut values).

Examples 14-16

Environmental Compatibility

Environmental experiments were performed to test biodegradation and toxicity. The biodegradation tests used the standard OECD Guideline for Testing of Chemicals TG 306 (Biodegradability in Seawater) 28 day method (version adopted 17 Jul. 1992) for testing biodegradation of chemicals in seawater.

Toxicity was tested against *Skeletonema costatum* and $EC_{50}$ values determined (over 72 hours). Results are presented in table 9.

TABLE 9

| Example | Composition | Toxicity $EC_{50}$ | Biodegradation after 28 days |
|---|---|---|---|
| Reference example 5 | TTPC | 0.016 mg/l | 11% |
| Example 14 | X3342-C14 | 1.9 mg/l | 51% |
| Example 15 | X3342 | 2.3 mg/l | 61% |
| Example 16 | X3622 | 2.4 mg/l | 51% |

Examples 14-16 all show both lower toxicity and improved biodegradability when compared with reference example 5 (TTPC). *Skeletonema costatum* $EC_{50}$ in all cases is less than 10 mg/l. The biodegradation data for examples 14-16 is much better than reference example 5; for example 15 the value exceeds 60%.

The invention claimed is:

1. A composition, useful for inhibiting gas hydrate formation during oil and gas exploration, recovery, or processing, said composition comprising:

a quaternary ammonium compound of formula (I)

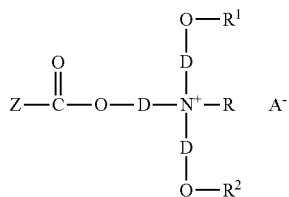

wherein:
R is a $C_{1-4}$ alkyl group, $C_{6-10}$ aryl group, or $C_{1-4}$alkyl-$C_{6-10}$ aryl group, poly($C_{2-4}$ alkylene oxide), or poly(styrene oxide), any of which may be substituted by one or more groups selected from halide, $C_{1-4}$ alkyl, —OH, —COOH, —C(=O)$C_{1-4}$alkyl, or $C_{1-4}$alkylene—OH;
$R^1$ is hydrogen or a group of formula —C(=O)X; and $R^2$ is hydrogen or a group of formula —C(=O)Y, provided that $R^1$ and $R^2$ are not both hydrogen;
X and Y are each independently a hydrogen, $C_{1-6}$ alkyl or $C_{1-6}$ alkenyl group;
Z is a $C_{4-24}$ alkyl or $C_{4-24}$ alkenyl group;
each D is independently a $C_1$ to $C_4$ alkylene group; and
$A^-$ is an anion, and
organic solvent, the organic solvent being an aromatic organic solvent or a mixtures of aromatic organic solvents.

2. A composition according to claim 1, wherein R is a methyl group or benzyl group.

3. A composition according to claim 1, wherein the groups X and Y are identical.

4. A composition according to claim 3, wherein X and Y are $C_3$ alkyl groups.

5. A composition according to claim 1, wherein Z is a $C_{7-17}$ alkyl group or —C(=O)Z is the acyl unit derived from a fatty acid selected from caprylic acid, capric acid, lauric acid, myristic acid, palmitic acid, stearic acid, oleic acid, erucic acid, linoleic acid, linolenic acid, ricinoleic acid, isostearic acid, isopalmitic acid, eicosanoic acid, gadoleic acid, palmitoleic acid, arachidonic acid, clupanadonic acid, and behenic acid.

6. A composition according to claim 1, wherein D is —$CH_2CH_2$—.

7. A composition according to claim 1, wherein the anion $A^-$ is selected from halides, methosulphate, methophosphate and ethosulphate.

8. A composition according to claim 1 in which the cation has formula II, III or IV.

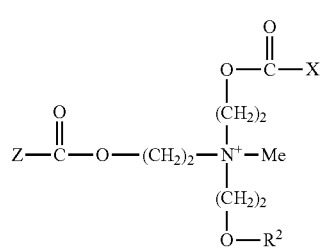

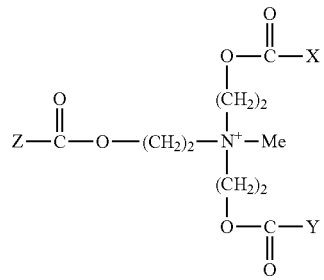

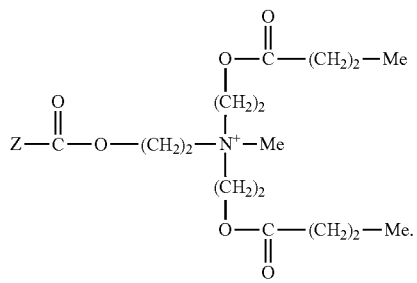

9. A composition according to claim 1 comprising a mixture of at least two quaternary ammonium compounds according to Formula I that differ at least in the identity of group —C(=O)Z.

10. A composition according to claim 9, wherein the ratio of different —C(=O)Z groups of the different quaternary ammonium compounds in the composition corresponds, to at least 90% correspondence, to the ratio of different carbon chain lengths in the acyl units of one of the mixtures of fatty acids selected from rapeseed oil fatty acids, soya oil fatty acids, tall oil fatty acids, tallow oil fatty acids, palm oil fatty acids, palm kernel oil fatty acids, coconut oil fatty acids, stripped coconut oil fatty acids, cottonseed oil fatty acids, wheat germ oil fatty acids, olive oil fatty acids, corn oil fatty acids, sunflower oil fatty acids, safflower oil fatty acids, and hemp oil fatty acids.

11. A composition according to claim 9, wherein at least 90% of the quaternary ammonium compounds in the composition have —C(=O)Z acyl groups with a carbon chain length selected from: $C_8$ and $C_{10}$; $C_{10}$ and $C_{12}$; $C_{12}$ and $C_{14}$; $C_{14}$ and $C_{16}$; $C_{16}$ and $C_{18}$; or $C_{18}$ and $C_{20}$.

12. A composition according to claim 1 comprising 10 to 99 volume percent of the quaternary ammonium compound according to Formula I and 1 to 90 volume percent of water, a water-miscible organic solvent, or both.

13. A composition according to claim 1 comprising 10 to 99 volume percent of the quaternary ammonium compound according to Formula I and 1 to 90 volume percent of the organic solvent.

14. A method of inhibiting gas hydrate agglomeration in a liquid, the method comprising contacting the liquid with a composition according to claim 1.

15. Use of a composition according to claim 1 as an anti-agglomeration hydrate inhibitor for an oil or gas processing application or a downhole application.

* * * * *